(12) United States Patent
Rotach et al.

(10) Patent No.: US 8,844,355 B2
(45) Date of Patent: Sep. 30, 2014

(54) LOAD RECEIVER DEVICE FOR DENSITY DETERMINATIONS

(75) Inventors: Hans-Jörg Rotach, Effretikon (CH); Alice Buchmann, Hinwill (CH)

(73) Assignee: Mettler-Toledo AG, Greifensee (CH)

( * ) Notice: Subject to any disclaimer, the term of this patent is extended or adjusted under 35 U.S.C. 154(b) by 728 days.

(21) Appl. No.: 13/029,832

(22) Filed: Feb. 17, 2011

(65) Prior Publication Data

US 2011/0197671 A1 Aug. 18, 2011

(30) Foreign Application Priority Data

Feb. 17, 2010 (EP) .................................. 10153763

(51) Int. Cl.
*G01N 9/00* (2006.01)
(52) U.S. Cl.
USPC ............................................................ 73/454
(58) Field of Classification Search
CPC ............. G01N 9/00; G01N 9/08; G01N 9/10; G01N 2009/00; G01N 2009/026
USPC ........................... 73/32 R, 433, 435, 451, 454
See application file for complete search history.

(56) References Cited

U.S. PATENT DOCUMENTS

| | | | | |
|---|---|---|---|---|
| 2,936,164 A * | 5/1960 | Di Giorgio | ..................... | 177/207 |
| 3,068,683 A * | 12/1962 | Petterson, Jr. et al. | ......... | 73/1.28 |
| 3,589,200 A * | 6/1971 | Nilsson | ........................... | 73/438 |
| 3,747,416 A * | 7/1973 | Wommack | ...................... | 73/437 |
| 4,372,405 A * | 2/1983 | Stuart | ......................... | 177/25.14 |
| 4,400,978 A * | 8/1983 | Guay et al. | ..................... | 73/453 |
| 4,770,041 A * | 9/1988 | Bearce | ............................ | 73/437 |
| 5,076,107 A | 12/1991 | Timmermans et al. | | |
| 6,561,025 B2 * | 5/2003 | Ueno | .............................. | 73/437 |
| 7,258,007 B2 * | 8/2007 | Galichet | ........................ | 73/437 |
| 7,296,466 B2 * | 11/2007 | Kusumoto | ..................... | 73/437 |
| 7,475,595 B1 * | 1/2009 | Tesch | ............................. | 73/437 |
| 2002/0117002 A1 * | 8/2002 | Ueno | .............................. | 73/437 |
| 2005/0210975 A1 * | 9/2005 | Kusumoto | ..................... | 73/437 |

FOREIGN PATENT DOCUMENTS

| | | |
|---|---|---|
| JP | 2002-243615 A | 8/2002 |
| JP | 2003-307482 A | 10/2003 |
| JP | 2008-180533 A | 8/2006 |

* cited by examiner

*Primary Examiner* — Peter Macchiarolo
*Assistant Examiner* — Samir M Shah
(74) *Attorney, Agent, or Firm* — Standley Law Group LLP (57) ABSTRACT

A load receiver device that serves to receive at least one solid body and to hold the solid body in place in a surrounding fluid during a density determination. Embodiments of the load receiver device include a hanger module that is adapted to establish a hanging connection to a part that is, in turn, connected to the weighing cell of a balance. Embodiments of the load receiver device further include a receiver module that is connected to the hanger module and serves to receive a solid body. The receiver module has a concavity that is designed to receive the solid body, and the orientation of the concavity can be selectively reversed to maintain the position of the solid body in the surrounding fluid during a density determination, regardless of whether the solid body will otherwise sink or float in the fluid.

20 Claims, 7 Drawing Sheets

Fig. 1 (Known Device)

Fig. 2 (Known Device)

LOAD RECEIVER DEVICE FOR DENSITY DETERMINATIONS

CROSS-REFERENCE TO RELATED APPLICATIONS

This application is entitled to, and claims, benefit of a right of priority under 35 USC §119 from European patent application 10153763.7, filed on 17 Feb. 2010, the content of which is incorporated by reference as if fully recited herein.

TECHNICAL FIELD

The present invention concerns load receiver devices adapted to receive at least one solid body that can be held inside a surrounding fluid during a density determination.

BACKGROUND

Load receiver devices according to the present invention are used primarily for the determination of the density of solid bodies. During the density determination, the solid body is held in a surrounding fluid which is inside a container that is not coupled to the weighing cell of the balance. The density determination can be performed with solid bodies that float as well as bodies that sink in the fluid. In the case of bodies that float, the density of the body is lower that the density of the surrounding fluid. In the case of bodies that sink, the density of the body is higher that the density of the surrounding fluid. In order to hold the solid bodies in the surrounding fluid, a load receiver device is needed.

A load receiver device for solid bodies that sink in the surrounding fluid belongs to the known state of the art. This load receiver device has a receiver module with a concavity. The depth of the concavity is oriented in the direction of gravity. A solid body that sinks in the surrounding fluid can be seated in this concavity and thereby be held in place in the fluid. This receiver module is not suitable for determining the density of bodies that float on the fluid, as the floating body will rise to the surface of the fluid. Therefore, an additional load receiver device is needed for the density determination of solid bodies that float in the test fluid. This load receiver device, which likewise belongs to the state of the art, has a receiver module with a concavity, wherein the depth of the concavity is oriented against the direction of gravity. The floating solid body is placed below the receiver module. The force of buoyancy acts on the floating body and pushes the latter from below into the concavity, whereby the body is held in place in the fluid.

These state-of-the-art load receiver devices have the disadvantage that different load receiver devices are required to determine the density of floating and sinking solid bodies, respectively.

This drawback has been eliminated by the load receiver device disclosed in U.S. Pat. No. 6,561,025 B2. This load receiver device includes a rigid flat grid which, in the density determination process, is positioned at a right angle to the direction of gravity. For the density determination of a body that sinks, the body is set on the grid. Then the load receiver device with the body on the grid is submerged in the fluid. The force of gravity acting on the body pushes the latter down against the grid, whereby the body is held in place in the surrounding fluid. For the density determination of a floating solid body, the body is likewise placed on the grid. To prevent the body from rising to the surface of the fluid, a buoyancy constraint is put over the body. The buoyancy constraint is configured so that the constraint and the grid together form a hollow enclosure in which the solid body is held in place during the density determination. To perform the density determination on the floating body, the load receiver device and the solid body, which is enclosed between the grid and the buoyancy constraint, are submerged in the fluid. Due to the buoyant force acting on it, the solid body is pushed against the buoyancy constraint and held in place in the fluid. The gravity force acting on the buoyancy constraint must be greater than the buoyant force acting on the solid body. This load receiver device has the disadvantage that an additional part, specifically a buoyancy constraint, is required for the density determination of solid bodies that float.

This disadvantage is circumvented in the load receiver device that is disclosed in U.S. Pat. No. 7,296,466 B2. The load receiver device as disclosed in this reference has a metallic tube with two ends and a flat bottom plate. In the process of a density determination, the axis of the tube is oriented in the direction of gravity. The bottom plate is held captive inside the tube with the freedom to move in the direction of gravity. When performing density determinations on solid bodies that sink in the fluid, the body is set on the bottom plate. Due to the gravity force acting on the body the bottom plate is pushed downwards. A first stop prevents the bottom plate from sliding out of the lower end of the tube. To determine the density of solid bodies that float, the body is placed below the bottom plate. Due to the gravity force acting on the body during the density determination the bottom plate is pushed in the upward direction. A second stop prevents the bottom plate from sliding out of the upper end of the tube. For the density determination of floating solid bodies, the buoyant force acting on the body needs to be strong enough to push the bottom plate upward against the force of gravity. If the density of the solid body is similar to the density of the fluid, the problem arises that the body cannot be reliably held in place in the fluid.

It is therefore an object of the present invention to provide a load receiver device that can be reliably used for the density determination of solid bodies with densities of any magnitude.

The load receiver device is particularly useful in determining the density of solid bodies having a density similar to that of the surrounding fluid.

SUMMARY OF THE GENERAL INVENTIVE CONCEPT

A load receiver device according to the present invention, serving to receive at least one solid body that may be held in place in a surrounding fluid during a density determination, includes a hanger module to establish a hanging connection to a part that is, in turn, connected to the weighing cell of a balance. The device further includes a receiver module that is connected to the hanger module and serves to receive the solid body. Furthermore, the receiver module has a concavity designed to receive the solid body, and the orientation of the concavity can be selectively set so that in a first operating position of the receiver module, a solid body that sinks in the fluid can rest in the concavity because of the gravity force acting on the body, and in a second operating position of the receiver module, a solid body that floats in the fluid can be held in place in the surrounding fluid by means of the concavity because of the buoyant force acting on the body.

A load receiver device according to the invention has the advantage that there are no parts that must be moved by either the gravity force or the buoyant force. Thus, the load receiver device may also be used in cases where there is only a small gravity force or only a small buoyant force acting on the solid body. It is also of advantage that no additional parts, such as for example a buoyancy constraint, are needed for the density determination of solid bodies that float in the surrounding fluid.

In one possible embodiment, the receiver module is pivotally mounted so that it can turn about an axis of rotation that runs perpendicular to the direction of gravity. By turning the receiver module about this axis of rotation, one can selectively flip between a first and a second operating position. This involves a turn of approximately 180°. In the first operating position, the bottom of the concavity is pointed in the direction of gravity during the density determination. In the second operating position, the bottom of the concavity is pointed in the direction of the buoyant force during the density determination.

The axis of rotation can run through the receiver module or through the rim of the receiver module. The receiver module is particularly stable, if the axis of rotation passes through two diametrically opposite points on the rim of the receiver module.

A load receiver device according to one possible embodiment has a height-adjusting element whereby the immersion depth of the receiver module into the surrounding fluid can be varied. The immersion depth is ideally selected so that in the first operating position (i.e., for a solid body that sinks in the fluid) there is enough space to immerse the body within the fluid above the receiver module, and in the second operating position (i.e., for a solid body that floats in the fluid) there is enough space within the fluid below the receiver module. It is advantageous to select a smaller immersion depth for the density determination of a solid body that floats than for a solid body that sinks in the surrounding fluid.

The height-adjusting element is ideally a part of the hanger module. Alternatively, an embodiment where the height-adjusting element is part of the receiver module is also possible.

Ideally, the vertical location of the axis of rotation relative to the receiver module during a density determination is such that in the first operating position the axis of rotation is located above the receiver module, and in the second operating position the axis of rotation is located below the receiver module. With this arrangement, the receiver module descends deeper into the surrounding fluid in the first operating position than it does in the second operating position. This has the advantage that in the second operating position (i.e., for density determinations of bodies that float) a taller space for the solid body is available in the fluid below the receiver module. In the first operating position (i.e., for density determinations of bodies that sink) a taller space for the solid body is available in the fluid above the receiver module. With an appropriate choice for the distance of the axis of rotation from the receiver module, the correct immersion depth of the receiver module in the surrounding fluid is automatically assured in both the first and the second position. Thus, an additional height-adjusting element becomes unnecessary.

It is advantageous if the load receiver device has at least one locking element that serves to releasably lock the receiver module in at least one of the two operating positions. In this manner, the solid body can be held in a positively defined position. It is easier to put the solid body in its place in the fluid if the receiver module is immobilized.

If the locking element includes means for a defined setting of the operating position, it is made simpler for the user to switch the receiver device into the required operating position.

One possible means for the defined setting of the operating position can consist of an indent and a spring that cooperate with each other. The spring may be part of the hanger module and the indent may be part of the receiver module. However, an arrangement is also conceivable where the spring is part of the receiver module and the indent is part of the hanger module. It is also possible that the hanger module as well as the receiver module may have a spring. Further conceivable is a design where an indent that works together with a part of the receiver module or the hanger module is recessed into the spring.

The hanger module, in one possible embodiment, has two rods for the fastening of the receiver module, and the receiver module has at least one indent. In this arrangement, at least one of the rods is bent into a spring that works together with an indent of the receiver module. However, the engagement is especially secure if both of the rods are bent into springs and for each of the springs there is cooperating indent in the receiver module.

The receiver module can include a tongue with a cutout, wherein the cutout forms the indent of the locking element.

As an alternative, the receiver module can have a tongue with two bent-out sections, wherein the indent of the locking element is formed by the bent-out sections. In this arrangement, a bent-out section is delimited by an outside contour edge and a fold-line edge. The fold-line edge borders on the indent.

Ideally, the locking element is self-centering. This can be realized with fold-line edges that run towards each other and outside contour edges that are smoothly curved. Each of the contour edges is shaped so that a rod can be guided in a sliding movement along the rounded contour into the indent. As a result, the rod can seat itself in a clearly defined position.

In an alternative embodiment, the receiver module may comprise a reversibly deformable material. The deformability of the receiver module is such that by applying a targeted force, the receiver module can snap reversibly between the first and the second operating position. The deformable material is an elastic spring material shaped to allow a switch between the two operating positions comparable to a clicker toy. This embodiment has the advantage that it requires no movable connection between the receiver module and the hanger module. The receiver module and the hanger module can be rigidly connected to each other. In this embodiment, the immersion depth of the receiver module does not change automatically in the switch between the first and second operating positions. An additional height-adjusting element is therefore normally required.

To prevent the formation of air pockets that could cause errors, the receiver module ideally has perforations that allow air to escape.

The surrounding fluid into which a receiver module of the present invention is immersed is normally a liquid, in most cases distilled water or ethanol.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
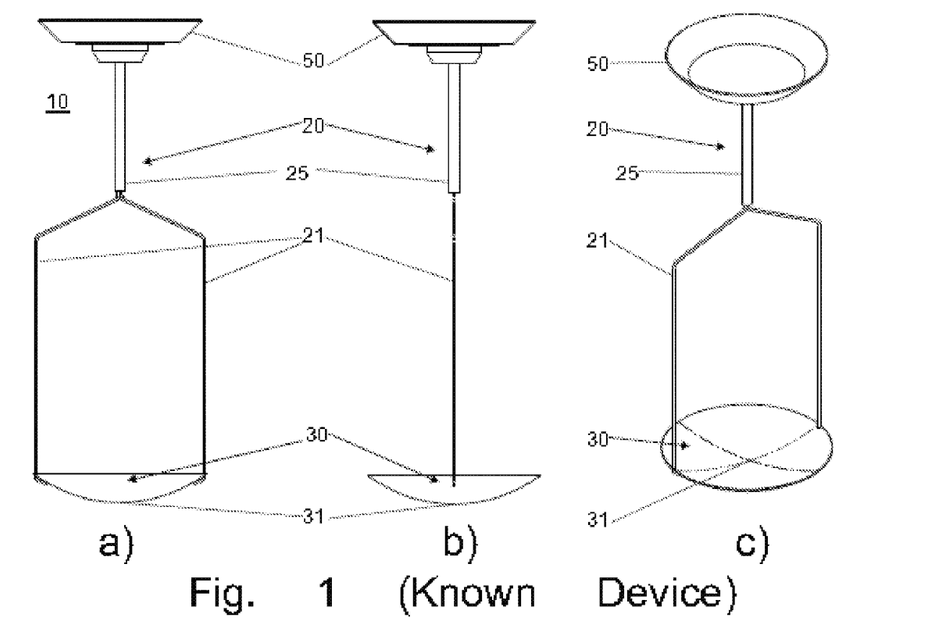
FIG. 1 shows a) a frontal view, b) a side view, and c) a perspective view of a known load receiver device for solid bodies that sink in the surrounding fluid.

FIG. 1 represents a) a frontal view, b) a side view, and c) a perspective view of a known load receiver device 10 for solid bodies that sink in the surrounding fluid. The load receiver device 10 includes a receiver module 30. The receiver module 30 consists, in essence, of a round surface which has a concavity 31. The receiver module 30 has a circular rim. The bottom of the concavity 31 points in the direction of gravity. The concavity 31 serves to receive at least one solid body which would sink in the surrounding fluid if not held in place by the receiver module 30 during a density determination. The solid body sinks in the surrounding fluid if the density of the solid body is greater than the density of the surrounding fluid.

The receiver module 30 is connected to a hanger module 20, which establishes a hanging connection to a part that is connected, in turn, to the weighing cell of a balance. The hanger module 20 includes two rods 21. One end of each rod 21 is rigidly connected to a point of the rim of the receiver module 30. The two points of connection between the hanger module 20 and the receiver module 30 are arranged substantially diametrically opposite each other on the circular rim of the receiver module 30. The two rods 21 are of substantially equal length, with the length of the rods 21 being selected so that in a density determination, a solid body lying on the receiver module 30 is completely immersed in the liquid.

At the opposite ends from the connections to the receiver module 30, the rods 21 are held together by a sleeve 25. The rods 21 as well as the sleeve 25 are oriented vertically during the density determination. The sleeve 25 is connected to a further receiver module 50 for the measurement outside of the liquid. The receiver module 50 for the measurement outside of the liquid is in essence a bowl which serves to receive at least one solid body. The receiver module 50 can be suspended from a stand that is connected to the weighing cell of a balance and has a horizontally oriented arm. The underside of the bowl can be seated on the arm of the stand.

Figure 2:
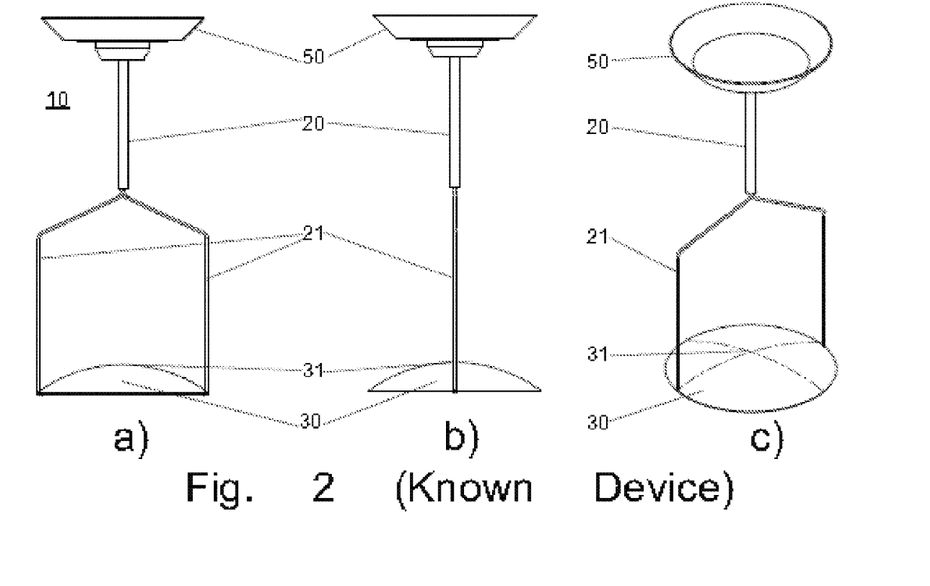
FIG. 2 shows a) a frontal view, b) a side view, and c) a perspective view of a known load receiver device for solid bodies that float in the surrounding fluid.

FIG. 2 represents a) a frontal view, b) a side view, and c) a perspective view of a further load receiver device 10 according to the state of the art for solid bodies that float in the surrounding fluid. The load receiver device 10 in FIG. 1 for sinking solid bodies has essentially the same features as the load receiver device 10 in FIG. 2. The differences are in the orientation of the concavity 31 of the receiver module 30 and in the length of the rods 21 of the hanger module 20. The concavity 31 is oriented in the direction of the buoyant force. In this arrangement, a solid body that floats in the surrounding fluid can be placed under the receiver module 30. As a result of the buoyant force acting on the solid body, the latter is pushed into the concavity 31 and thereby held in place in the surrounding fluid. In order to allow enough space to accommodate the solid body in the surrounding fluid, the rods 21 need to be shorter than in the load receiver device for sinking solid bodies.

Figure 3:
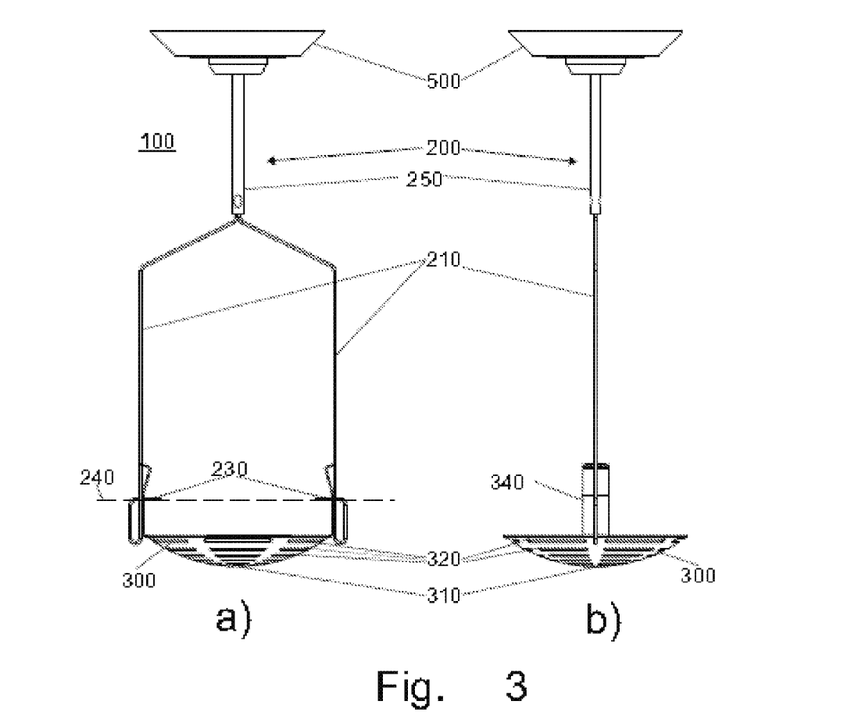
FIG. 3 shows a) a frontal view and b) a side view of one exemplary embodiment of a load receiver device of the present invention, with a rotatably supported receiver module in a first operating position.

FIG. 3 shows a) a frontal view and b) a side view of a first exemplary embodiment of a load receiver device 100 of the present invention with a rotatably supported receiver module 300 in the first operating position. This load receiver device 100 has some of the same components as the known load receiver devices 10 of the state of the art in FIGS. 1 and 2. The significant difference between the load receiver device 100 and the known load receiver devices 10 lies in the connection between the hanger module 200 and the load receiver module 300. More specifically, in this embodiment of the present invention, the load receiver module 300 is pivotally supported with the ability to turn about an axis of rotation 240. In both operating positions, the axis of rotation 240 is oriented horizontally during the density determination.

In the first operating position (i.e., for the density determination of a solid body 900 that sinks in the surrounding fluid), the axis of rotation 240 is located above the receiver module 300. Two tongues 340 are attached to the rim of the receiver module 300 at two substantially diametrically opposite points. The tongues 340 are rigidly connected to the receiver module 300. During the density determination, the two tongues 340 have a substantially vertical orientation. The tongues 340 are of an elongated shape and have two ends. A first end of each tongue 340 is connected to the receiver module 300. The tongue 340 is shaped so that the second end of the tongue 340 is directed horizontally. The edge of the second end has an indent 421 which serves to engage one of the rods 210 of the hanger module 200. The indent 421 is arranged so that the receiver module can be locked in the first or the second operating position. Each tongue 340 further contains a bearing 330 in the form of a hole which serves to receive the end of one of the rods 210 of the hanger module 200. To allow the bearing 330 to receive the end of the rod 210, the end of the rod 210 that connects to the receiver module 300 has to be bent in such a way that in its operating position it will be directed horizontally and can be inserted into the bearing 330. The horizontally directed ends of the rods 210 define the axis of rotation 240 where the receiver module 300 is rotatably supported.

Each of the rods 210 of the hanger module 200 is bent into a spring 410, so that the spring tension generated in each rod 210 pushes the latter into the corresponding indent 421. This serves as an additional means to secure the receiver module 300 in either of the first and second operating positions.

If occluded air bubbles were inadvertently picked up during the density determination, this will cause errors in the result of the measurement. The receiver module 300 therefore has perforations 320 which counteract the occlusion of air bubbles during the density determination.

Figure 4:
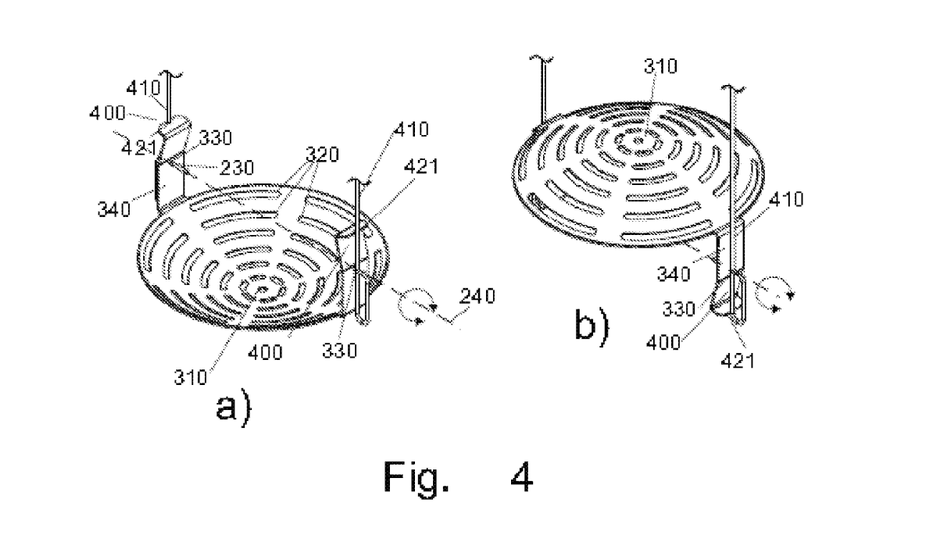
FIG. 4 shows perspective views of a detail of the load receiver device of FIGS. 3a)-3b) according to the invention in a) the first operating position and b) a second operating position.

FIG. 4 shows isometric views of a detail of the first embodiment of the load receiver device 100 according to the invention in the first and second operating position, respectively. The pins 230 (rod ends) of the hanger module 200 that form the axis of rotation 240 are located above the receiver module 300 when the latter is in the first operating position. If the receiver module 300 is flipped over from the first operating position by 180° about the axis of rotation 240, it will occupy the second operating position where the axis of rotation 240 is located below the receiver module 300. As shown, the interaction between the rods 210 and the indents 421 of the tongues 340, allows each tongue to function as a lock element 400 that maintains the operating position of the receiver module 300.

With the arrangement of the axis of rotation 240 that has just been described, the immersion depth of the receiver module 300 in the surrounding liquid 1000 (see FIGS. 13-14) is automatically changed. In the first operating position, where the solid body 900 (see FIGS. 13-14) is resting on the receiver module 300, the receiver module 300 is immersed deeper than in the second operating position where the solid body 900 pushes from below against the receiver module 300. As a result of the variable immersion depth, there is enough space available in the first operating position to accommodate the solid body 900 on top of the receiver module 300 and in the second operating position to accommodate the solid body 900 below the receiver module 300.

Figure 5:
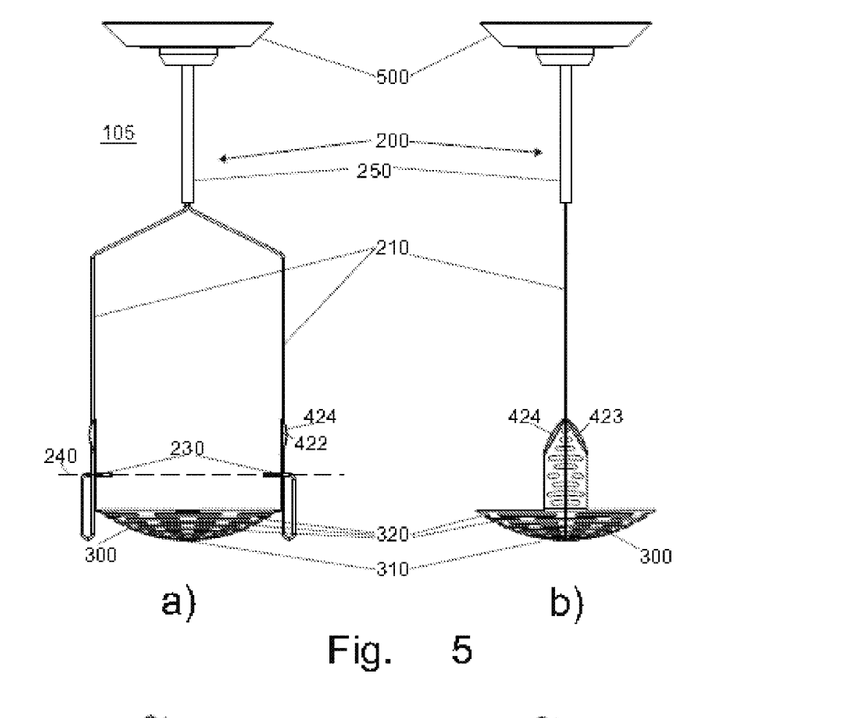
FIG. 5 shows a) a frontal view and b) a side view of another exemplary embodiment of a load receiver device according to the present invention in a first operating position.
Figure 6:
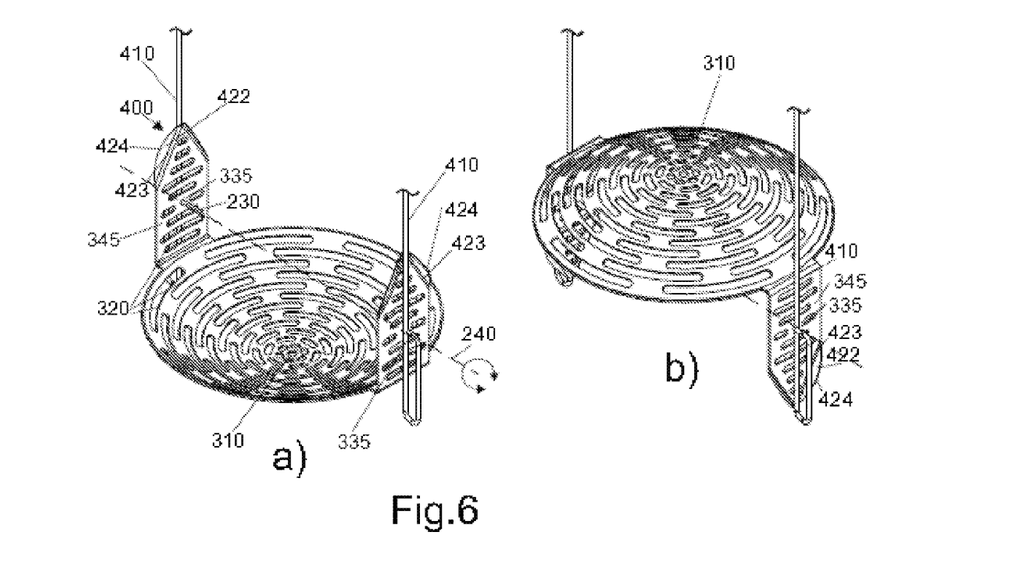
FIG. 6 shows perspective views of a detail of the load receiver device of FIGS. 5a)-5b) in a) the first operating position and b) a second operating position.

FIG. 5 represents a frontal view and a side view of a second embodiment of a load receiver device 105 according to the present invention in a first operating position. FIG. 6 shows isometric views of a detail of the second embodiment of the load receiver device 105 according to the invention in the first and a second operating position, respectively.

The second embodiment differs from the first embodiment of FIGS. 3 and 4 essentially in the design of the tongues. The tongues 345 of this embodiment have a substantially vertical orientation during the density determination. A first end of each tongue 345 is connected to the receiver module 300. The second end has an indent which serves to receive one of the rods 210 of the hanger module 200. The indent is formed by a first and a second bent-out section 422 of the tongue 345. The bent-out sections 422 are produced by folding the tongue 345 along the first and second fold-line edges 423. The fold-line edges are angled against each other in a V-shape towards the second end of the tongue 345. The two fold-line edges do not meet but leave enough space between them to seat a rod 210 of the hanger module 200. Both the first and the second bent-out section 422 have rounded outside contours 424.

When switching from one operating position to the other, a rod 210 of the hanger module 200 can slide along the rounded contour 424. As the rods are bent into springs 410, exactly as in the first embodiment, the rods 210 are under tension and are pushed against the tongues 345. In the position change, the rod 210 of the hanger module 200 is guided along the round contour 424 until the rod 210 is seated in the indent. As the rod 210 is under tension due to the spring 410 the rod 210 snaps into the indent, allowing the tongue 345 to act as a locking element 405. Each tongue 345 again contains a bearing 335 in the form of a hole which serves to receive the end of one of the rods of the hanger module 200.

The tongue 345 of the second embodiment has a larger surface area in comparison to the tongue 340 of the first embodiment. This larger surface entails an increased risk of occluded air bubbles which introduce errors. This problem is alleviated by the perforations 320 in the tongue 345.

Figure 7:
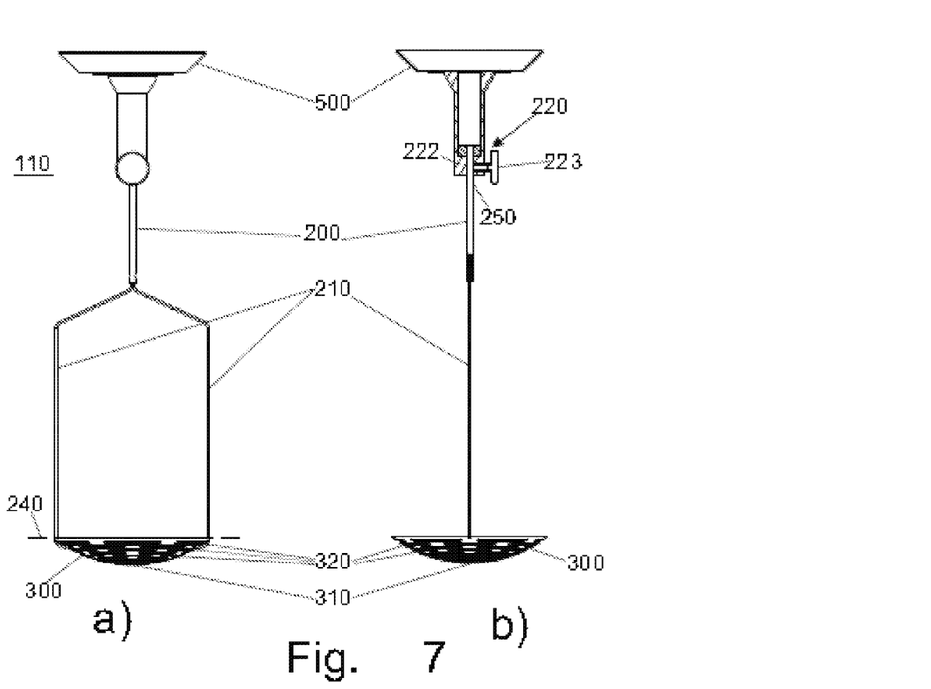
FIG. 7 shows a) a frontal view and b) a side view of another exemplary embodiment of a load receiver device according to the present invention in a first operating position.
Figure 8:
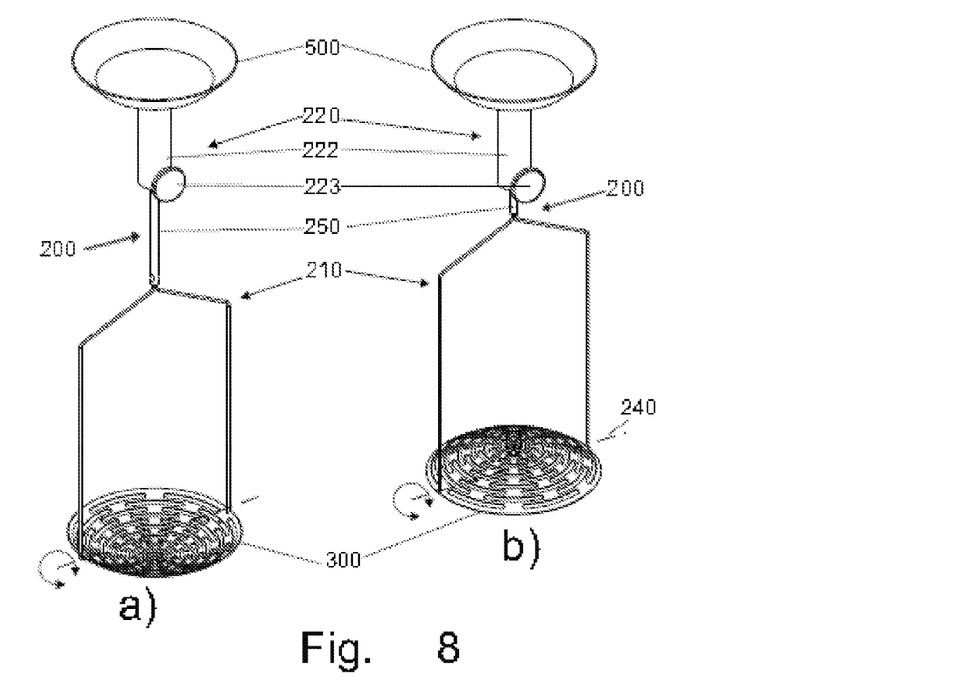
FIG. 8 shows perspective views of the load receiver device of FIGS. 7a)-7b) in a) the first operating position and b) a second operating position.

FIG. 7 represents a frontal view and a side view of a third embodiment of a load receiver device 110 according to the present invention in a first operating position. FIG. 8 shows isometric views of the third embodiment of the load receiver device 110 according to the invention in the first and a second operating position, respectively. This third embodiment differs from the first and second embodiments in that the axis of rotation 240 in the third embodiment lies in the same horizontal plane as the rim of the receiver module 300. In contrast to the first and second embodiments, the immersion depth of the receiver module 300 of the third embodiment therefore does not change with the operating position. This means that the same immersion depth is maintained for the first and second operating positions. However, as has already been described, it is advantageous if the receiver module 300 in its first operating position is immersed more deeply in the surrounding fluid 1000 than in the second operating position.

The hanger module 200 therefore has a height-adjusting element 220 whereby the immersion depth of the receiver module 300 in the surrounding fluid 1000 can be regulated. As part of the height-adjusting element 220, the two rods 210 of the hanger module 200 are joined together in a sleeve 250 that is oriented vertically in the operating position. The sleeve 250 is seated inside a slide bushing 222, so that the sleeve 250 in its operating position can be slid vertically up and down in the bushing 222. In this way, the immersion depth of the receiver module 300 in the fluid 1000 may be regulated. The sleeve 250 is connected to a receiver module 500 that serves to measure the dry weight of the solid body. By means of a locking screw 223 the sleeve 250 can be secured in the slide bushing 222 at a suitable height.

Furthermore, the third embodiment as shown here does not include a locking element to secure the receiver module 300 in the first or the second operating position. However, due to either the buoyant force or the gravity force acting on the solid body 900, the receiver module 300 will still be held in place in the correct respective operating position.

Figure 9:
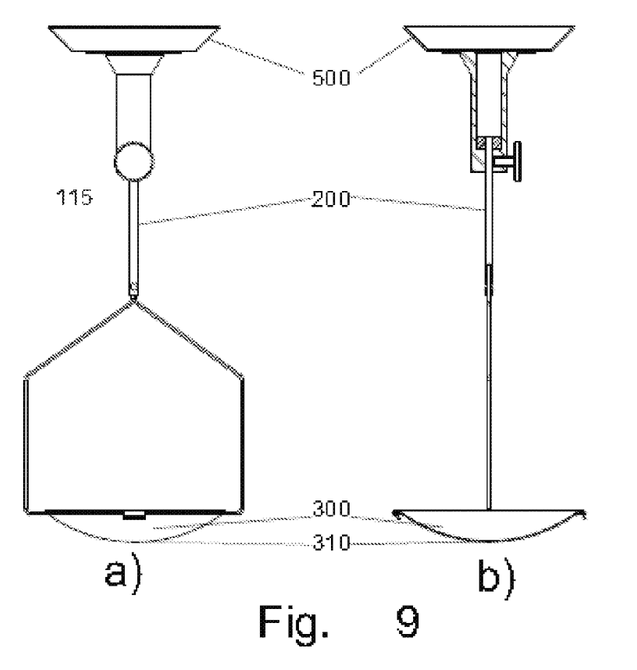
FIG. 9 shows a) a frontal view and b) a side view of another exemplary embodiment of a load receiver device according to the present invention in a first operating position.
Figure 10:
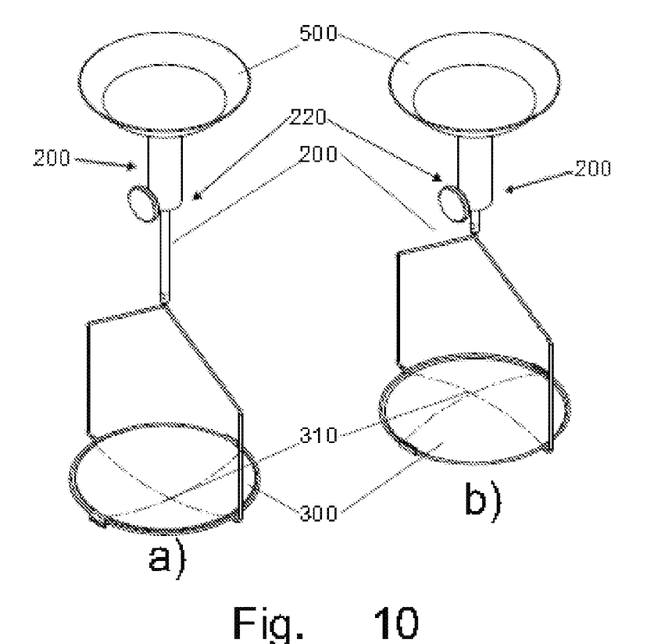
FIG. 10 shows perspective views of the load receiver device of FIGS. 9a)-9b) in a) the first operating position and b) a second operating position.

FIG. 9 shows a frontal view and a side view of a fourth embodiment of a load receiver device 115 according to the present invention in a first operating position. FIG. 10 shows isometric views of the fourth embodiment of the load receiver device 115 according to the invention in the first and a second operating position, respectively. The hanger module 200 and the receiver module 300 in this embodiment are not pivotally connected to each other. Instead, the change of orientation of the receiver module concavity 310 is achieved with a reversibly deformable receiver module 300 material. Consequently, the receiver module 300 may be switched between the first and the second operating position by applying a sufficient force thereto. The switching effect between the two positions is comparable to a clicker toy. In this embodiment, the immersion depth of the receiver module 300 in the surrounding fluid 1000 is regulated by means of a height-adjusting element 220.

Figure 11:
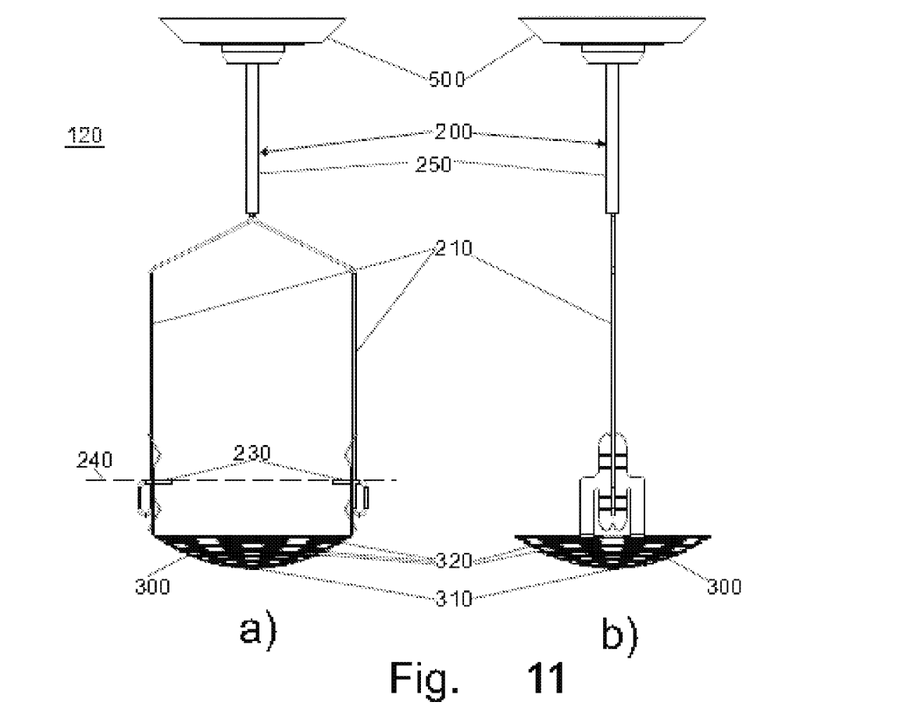
FIG. 11 shows a) a frontal view and b) a side view of another exemplary embodiment of a load receiver device according to the present invention in a first operating position.
Figure 12:
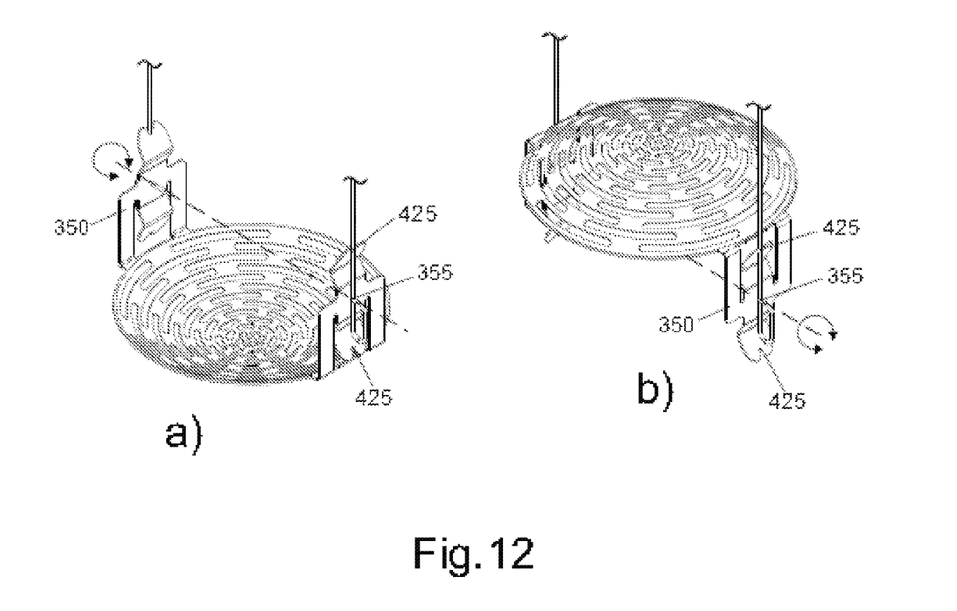
FIG. 12 shows perspective views of the load receiver device of FIGS. 11a)-11b) in a) a first operating position and b) the second operating position.

FIG. 11 shows a frontal view and a side view of a fifth embodiment of a load receiver device 120 according to the present invention in a first operating position. FIG. 12 shows isometric views of the fifth embodiment of the load receiver device 120 according to the invention in the first and a second operating position, respectively. This fifth embodiment is distinguished from the first embodiment shown in FIGS. 3 and 4 essentially by the design of the tongues. Each tongue 350 of this embodiment has two indents 425. The first indent serves to engage a rod 210 of the hanger module 200 in the first operating position. The second indent serves to engage the rod of the hanger module 200 in the second operating position. The axis of rotation 240 is located between the first and the second indent. Ideally, but not essentially, the first and the second indent are equidistant from the axis of rotation 240. Thus, in the first and the second operating position, the same point on the rod 210 is pushed by the spring force into the corresponding indent. Consequently, the rod 210 presses against one or the other of the indents 425 with an equal spring force in either of the two operating positions.

This design has the following advantage over the first embodiment. In the first and second operating positions, the one indent 425 in the first embodiment cooperates, respectively, with different parts of the rod 210. Consequently, the amount of spring force acting on the one indent 425 is different for the two operating positions. More specifically, the spring force acting on the indent 425 is of a smaller magnitude in the second operating position than in the first operating position and, accordingly, the receiver module 300 is less firmly secured in the second operating position than it is in the first operating position. As with some of the previous embodiments, each tongue 350 contains a bearing 355 in the form of a hole which serves to receive the end of one of the rods of the hanger module 200.

Figure 13:
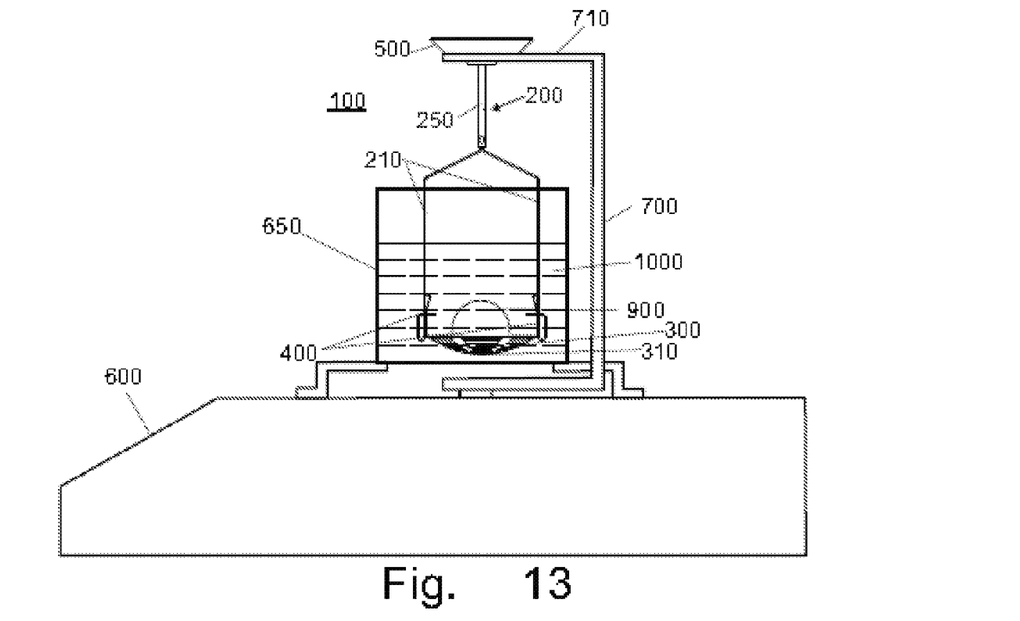
FIG. 13 shows a side view of a balance with the load receiver device of FIGS. 3a)-3b) in the first operating position for the density determination of solid bodies that sink in the surrounding fluid.

FIG. 13 represents a side view of a balance 600 with the first embodiment of the load receiver device 100 according to the invention in the first operating position for the density determination of solid bodies 900 that sink in the surrounding fluid. A container 650 holding a fluid 1000 is set up on the balance 600, but not functionally connected to the weighing cell. The fluid 1000 is preferably a liquid such as for example distilled water or ethanol. Connected to the weighing cell of the balance 600 is a stand 700 with a substantially horizontal cantilever arm 710. The cantilever arm 710 is located above the balance 600 and the container 650. The arm 710 of the stand 700 is designed so that the load receiver device can be attached thereto. Ideally, the hanger module 200 of the load receiver device 100 can be suspended from the cantilever arm 710. The load receiver device 100 has a receiver module 300 with a concavity 310 in which lies a solid body 900 that would sink in the surrounding fluid 1000. In this way, the solid body 900 is held in place in the fluid 1000.

Figure 14:
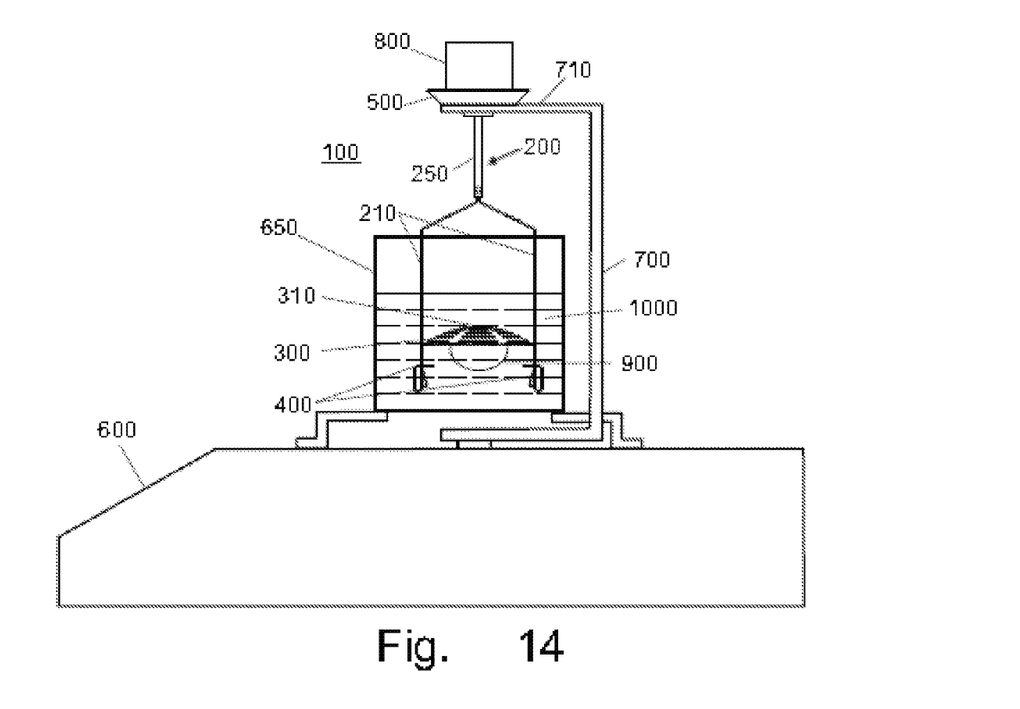
FIG. 14 shows a side view of a balance with the load receiver device of FIGS. 3a)-3b) in the second operating position for the density determination of solid bodies that float in the surrounding fluid.

FIG. 14 represents a side view of a balance 600 with the load receiver device 100 according to the invention as shown in FIG. 11 in the second operating position for the density determination of solid bodies 900 that float in the surrounding fluid. In this case, the density of the solid body 900 is less than the density of the surrounding liquid 1000. As a result of the buoyant force acting on the body 900, the latter is pushed into the concavity 310 of the receiver module 300. In this way, the solid body 900 is held in place in the fluid 1000.

To prevent the load receiver device 1000 from being pushed up by the buoyant force acting on the floating solid body 900, an additional weight 800 may be put into the dry-weight receiver module 500.

Although the invention has been described by presenting specific exemplary embodiments, it is evident that numerous further variant solutions could be created from knowledge of the present invention, for example by combining features of the individual exemplary embodiments with each other and/or by interchanging functional units between different exemplary embodiments.

LIST OF REFERENCE SYMBOLS 10, 100, 105, load receiver device
110, 115, 120
20, 200 hanger module
21, 210 rod
220 height-adjusting element
222 bushing
223 locking screw
230 pin
240 axis of rotation
25, 250 sleeve
30, 300 receiver module for weighing inside the liquid
31, 310 concavity
320 perforations
330, 335, 355 bearing (hole)
340, 345, 350 tongue
400, 405 locking element
410 spring
421 indent, cutout
422 bent-out section
423 fold-line edge
424 rounded contour
425 indent
50, 500 receiver module for weighing outside of the liquid
600 balance
650 container
700 stand
710 cantilever arm
800 weight
900 solid body
1000 surrounding liquid

What is claimed is:

1. A load receiver device that serves to receive at least one solid body and to hold said at least one solid body in place in a surrounding fluid during a density determination, the load receiver device comprising:

a hanger module adapted to establish a hanging connection to a part that is, in turn, adapted for connection to the weighing cell of a balance; and a receiver module that is connected to the hanger module and serves to receive a solid body, the receiver module having a concavity designed to receive a solid body, the orientation of the concavity being selectable so that in a first operating position a solid body that will sink in the surrounding fluid will be supported by the receiver module and retained in the concavity during a density determination by the force of gravity acting on the body, and in a second operating position of the receiver module a solid body that will float in the surrounding fluid will be held in place by the receiver module and retained in the concavity during a density determination by the buoyant force of the surrounding fluid acting on the body.

2. A load receiver device according to claim 1, wherein the receiver module is rotatably supported on the hanger module and able to turn about an axis of rotation that is oriented substantially perpendicular to the direction of the force of gravity, the receiver module adapted to be selectively flipped between the first and second operating positions by rotating the receiver module about the axis of rotation.

3. A load receiver device according to claim 2, wherein the axis of rotation runs through the receiver module.

4. A load receiver device according to claim 2, wherein the axis of rotation is arranged at a vertical distance from the receiver module such that in the first operating position the axis of rotation is located above the receiver module, and in the second operating position the axis of rotation is located below the receiver module.

5. A load receiver device according to claim 2, further comprising at least one locking element that is operable to releasably lock the receiver module in at least one of the two operating positions.

6. A load receiver device according to claim 5, wherein the locking element includes a spring that cooperates with at least one indent.

7. A load receiver device according to claim 6, wherein the spring is a part of the hanger module and the at least one indent is a part of the receiver module.

8. A load receiver device according to claim 7, wherein the hanger module comprises two rods to which the receiver module is attachable, and wherein at least one of the rods is bent into a spring that cooperates with at least one indent of the receiver module.

9. A load receiver device according to claim 7, wherein the receiver module comprises a tongue with a cutout, and wherein the cutout forms an indent of the locking element.

10. A load receiver device according to claim 7, wherein the receiver module comprises a tongue with a bent-out section that forms an indent of the locking element.

11. A load receiver device according to claim 7, wherein the receiver module comprises a tongue with a bent-out section that forms an indent of the locking element.

12. A load receiver device according to claim 1, wherein the receiver module includes perforations to prevent the accumulation of air pockets.

13. A balance in combination with the load receiver device of claim 1, the hanger module of the load receiver device directly or indirectly connected to a weighing cell of the balance.

14. A load receiver device that serves to receive at least one solid body and to hold said at least one solid body in place in a surrounding fluid during a density determination, the load receiver device comprising:
   a hanger module adapted to establish a hanging connection to a part that is, in turn, adapted for connection to the weighing cell of a balance; and
   a receiver module that is connected to the hanger module and serves to receive a solid body, the receiver module having a concavity designed to receive a solid body, the orientation of the concavity being selectable so that in a first operating position a solid body that will sink in the surrounding fluid will be supported by the receiver module and retained in the concavity during a density determination by the force of gravity acting on the body, and in a second operating position of the receiver module a solid body that will float in the surrounding fluid will be held in place by the receiver module and retained in the concavity during a density determination by the buoyant force of the surrounding fluid acting on the body;
   wherein the receiver module is pivotally supported and able to turn about an axis of rotation that is oriented substantially perpendicular to the direction of the force of gravity, and adapted to be selectively flipped between the first and second operating positions by rotating the receiver module about the axis of rotation; and
   wherein the receiver module further includes at least one locking element that is operable to releasably lock the receiver module in at least one of the first and second operating positions.

15. A load receiver device according to claim 14, wherein the axis of rotation runs through the receiver module.

16. A load receiver device according to claim 14, wherein the axis of rotation is arranged at a vertical distance from the receiver module such that in the first operating position the axis of rotation is located above the receiver module, and in the second operating position the axis of rotation is located below the receiver module.

17. A load receiver device according to claim 14, wherein the locking element includes a spring that cooperates with at least one indent.

18. A load receiver device according to claim 17, wherein the spring is a part of the hanger module and the at least one indent is a part of the receiver module.

19. A load receiver device according to claim 18, wherein the hanger module comprises two rods to which the receiver module is attachable, and wherein at least one of the rods is bent into a spring that cooperates with at least one indent of the receiver module.

20. A load receiver device according to claim 18, wherein the receiver module comprises a tongue with a cutout, and wherein the cutout forms an indent of the locking element.

* * * * *

UNITED STATES PATENT AND TRADEMARK OFFICE
CERTIFICATE OF CORRECTION

| | | |
|---|---|---|
| PATENT NO. | : 8,844,355 B2 | Page 1 of 1 |
| APPLICATION NO. | : 13/029832 | |
| DATED | : September 30, 2014 | |
| INVENTOR(S) | : Rotach et al. | |

It is certified that error appears in the above-identified patent and that said Letters Patent is hereby corrected as shown below:

On the title page, item (75), please delete "Alice Buchmann, Hinwill (CH)" and insert -- Alice Buchmann, Hinwil (CH) --.

Signed and Sealed this
Thirtieth Day of December, 2014

Michelle K. Lee
*Deputy Director of the United States Patent and Trademark Office*